United States Patent [19]

Katsuzaki

[11] Patent Number: 5,272,912
[45] Date of Patent: Dec. 28, 1993

[54] APPARATUS AND METHOD FOR MEASURING VISCOSITIES OF LIQUIDS

[75] Inventor: Nobuo Katsuzaki, Tokyo, Japan

[73] Assignee: Yayoi Co., Ltd., Tokyo, Japan

[21] Appl. No.: 986,130

[22] Filed: Dec. 4, 1992

[30] Foreign Application Priority Data

Mar. 30, 1992 [JP] Japan ................. 4-074322

[51] Int. Cl.⁵ ........................................... G01N 11/06
[52] U.S. Cl. ................................. 73/54.08; 73/54.09
[58] Field of Search .................. 73/54.07, 54.08, 54.09, 73/54.13

[56] References Cited

U.S. PATENT DOCUMENTS

| 3,286,511 | 11/1966 | Harkness | 73/54.07 |
| 3,435,665 | 4/1969 | Tzentis | 73/54.13 |
| 3,548,638 | 12/1970 | Uchida et al. | 73/54.09 |
| 3,604,247 | 9/1971 | Gramain et al. | 73/54.08 |

FOREIGN PATENT DOCUMENTS

| 3237130 | 4/1984 | Fed. Rep. of Germany | 73/54.09 |
| 298135 | 12/1988 | Japan | 73/54.08 |
| 3-127248 | 12/1991 | Japan. | |
| 616559 | 7/1978 | U.S.S.R. | 73/54.09 |
| 2233461 | 1/1991 | United Kingdom | 73/54.09 |

Primary Examiner—Hezron E. Williams
Assistant Examiner—Joseph W. Roskos
Attorney, Agent, or Firm—Koda and Androlia

[57] ABSTRACT

An apparatus for measuring viscosities of liquids has a narrow tube for a test liquid to be flowed. A differential pressure is generated between upstream and downstream of the test liquid. A differential pressure is measured at each divided time period for a total pass-by period which is a time for the test liquid to pass from a first to a second positions in the narrow tube. An integrated quantity obtained by determining a product of each divided time period and the differential pressure over the total pass-by period. Viscosity of the test liquid is obtained by comparing the integrated quantity with a corresponding integrated quantity previously determined in a reference sample liquid of known viscosity.

7 Claims, 5 Drawing Sheets

APPARATUS AND METHOD FOR MEASURING VISCOSITIES OF LIQUIDS

BACKGROUND OF THE INVENTION

The present invention relates generally to apparatuses and methods for measuring the viscous nature or viscosities of liquids and more particularly to a liquid viscometric apparatus and method in which viscosities of liquids of unknown viscosities (hereinafter referred to as "test liquids") are measured by causing these test liquids to flow through thin or narrow tubes.

Heretofore, in the viscometry of liquids, the values of the liquid viscosities have been determined from the liquid flow velocity and from the liquid resistance to flow. The principal methods of determining liquid viscosity values from liquid flow velocity are (1) the narrow tube method and (2) the steel ball fall method. Those of determining viscosity values from resistance are (3) the planar laminar flow method, (4) the coaxial cylinder rotation method, and (5) the cone-flat plate rotation method.

These methods have not been fully satisfactory for the following reasons. In the case of method (1), the measuring procedure requires much time since falling velocity is measured. In the case of method (2), measurement of a sample of small quantity is difficult. In the cases of methods (3) and (4), the properties of the liquid being measured undergo change because force from the outside is applied to the liquid. Furthermore, by the narrow tube method (1), because viscosity is determined from the resistance of the liquid, measurement of liquids of low viscosities is troublesome.

As means for overcoming the above described difficulties encountered in the prior art, a liquid viscometric apparatus has been previously proposed as disclosed in Japanese Utility Model Laid-Open publication No. 03-127248 (1991). In this viscometric apparatus, a narrow or thin tube such as a capillary tube is used in a circuit through which the liquid being measured is caused to flow. In the operation of this apparatus, the resistance to flow of the test liquid thus flowing through the narrow tube is not utilized. Instead, the time for the test liquid flowing through the capillary tube to move from a first point at an upstream position to a second point at a downstream position is measured, and the viscosity is calculated from this measured time. Moreover by changing the inner diameter of the capillary tube, measurement of low to high viscosities is made possible. Furthermore, in order to shorten the measurement time, differential pressure of positive pressure or negative pressure is applied to the flowing liquid.

In this previously proposed liquid viscometric apparatus described above, the time for the test liquid to travel from the above mentioned upstream first point to the downstream second point varies depending on a set suction pressure and other factors. For this reason, the measurement and computation of the viscosity in each case are carried out on the premise that differential pressure between the upstream and downstream sides of the liquid being measured is constant throughout the time period for the liquid to move from the above mentioned first point to the second point.

However it is not easy to fix this differential pressure at a set suction pressure or the like. Furthermore, even if this differential pressure could be maintained at a set suction pressure or the like, it cannot be readily reproduced accurately and positively.

Because of the nature of the method and apparatus for measuring the viscosities of liquids as described above, even a minute variation of the differential pressure of the liquid between the upstream and downstream sides causes a variation in the measured time for movement of the liquid from the first to the second points. Thus there has been the problem of error in the measured time value.

SUMMARY OF THE INVENTION

Accordingly, it is a general object of this invention to provide a liquid viscometric apparatus in which the above described problems have been solved, and which has high measurement accuracy and reliability.

It is another object of this invention in another aspect thereof to provide a method of measuring the viscosities of liquids.

According to the present invention in one aspect thereof there is provided an apparatus for measuring viscosities of liquids which comprises: conduit means forming a flow path for a test liquid whose viscosity is to be measured; a narrow tube for measurement constituting an intermediate part of the conduit means and having upstream and downstream sides with respect to the flow path; first and second detecting means for detecting the passing by of a specific part of the test liquid respectively past first and second positions in the narrow tube for measurement respectively near upstream and downstream ends thereof and for generating detection signals corresponding to the passing by; differential pressure means for creating a differential pressure of the test liquid between the upstream and downstream sides; pressure measuring means for measuring the differential pressure and generating a signal corresponding to the differential pressure at each instance of measurement; flow rate computing means for computing an integrated quantity obtained by computing the total pass-by period for the specific part of the test liquid to flow between the first and second positions in response to the detection signals generated by the first and second detecting means, by dividing the total pass-by period into a plurality of divided time periods, by determining the product of each divided time period and the differential pressure thus measured in that divided time period in response to the signal generated by the pressure measuring means, and by integrating the products thus determined over the total pass-by period; and viscosity computing means for computing the viscosity of the test liquid by comparing the integrated quantity with a corresponding integrated quantity previously determined by the flow rate computing means under the same conditions with respect to a reference sample liquid of known viscosity.

In a preferred embodiment of the invention, the above described apparatus preferably has the following features.

1. A tubular flow path for retention of coil shape for maintaining the test liquid at a uniform temperature constitutes the flow path upstream from the narrow tube for measurement. This tubular flow path is imbedded in a thermostatic means.

2. The above described tubular flow path for retention is made of a flexible material.

3. The tubular flow path for retention is made of a material of low reactivity.

4. The inner diameter of the flow path through which the test liquid travels increases in the upstream direction from the tubular flow path for retention.

Furthermore this inner diameter of the flow path increases also in the downstream direction from the tubular flow path for retention.

According to this invention in another aspect thereof, there is provided a method of measuring the viscosities of liquids which comprises: placing a test liquid whose viscosity is to be measured in a flow path formed by conduit means including at an intermediate portion thereof a narrow tube for measurement having upstream and downstream sides thereof with respect to the flow path; applying a differential pressure to the test liquid between the upstream and downstream sides of the narrow tube for measurement thereby to cause the test liquid to flow through the narrow tube from the upstream side to the downstream side thereof; measuring the total pass-by time period for the test liquid to pass by a second position on the downstream side after passing by a first position on the upstream side; dividing the total pass-by time period into a plurality of divided time periods; measuring the differential pressure during each of the divided time periods; determining the product of each divided time period and the differential pressure measured in that divided time period; integrating the products thus determined over the total pass-by time period thereby to obtain an integrated quantity; and computing the viscosity of the test liquid by comparing the integrated quantity thus obtained with a corresponding integrated quantity previously determined under the same conditions with respect to a reference sample liquid of known viscosity.

A preferred feature of the present invention is that the above described differential pressure is increased with increasing estimated value of the viscosity of the test liquid.

In accordance with the present invention, a differential pressure is created in the test liquid across the upstream and downstream sides of the narrow tube for measurement by the differential pressure means. Then, as the test liquid flows through the narrow tube for measurement, the differential pressure is measured by a pressure measuring means during each of incrementally divided time periods of the total time required by a leading part or a trailing part of the test liquid to pass by a second position at the downstream end of the narrow tube for measurement after passing by a first position at the upstream end of the narrow tube. By a flow rate computing means, the product of each divided time period and the differential pressure measured during that divided time period is determined, and the products thus determined are integrated over the total pass-by time to obtain an integrated quantity. It has been verified by experiments that this integrated quantity is substantially proportional to the viscosity of the liquid. Accordingly, this integrated quantity is compared by a viscosity computing means with a corresponding integrated quantity obtained previously under the same conditions with respect to a reference sample liquid of known viscosity thereby to compute the viscosity of the test liquid.

The nature, utility, and further features of the present invention will become more clearly apparent from the following detailed description with respect to a preferred embodiment of the invention when read in conjunction with the accompanying drawings briefly described below.

DESCRIPTION OF THE PREFERRED EMBODIMENT

Figure 1:
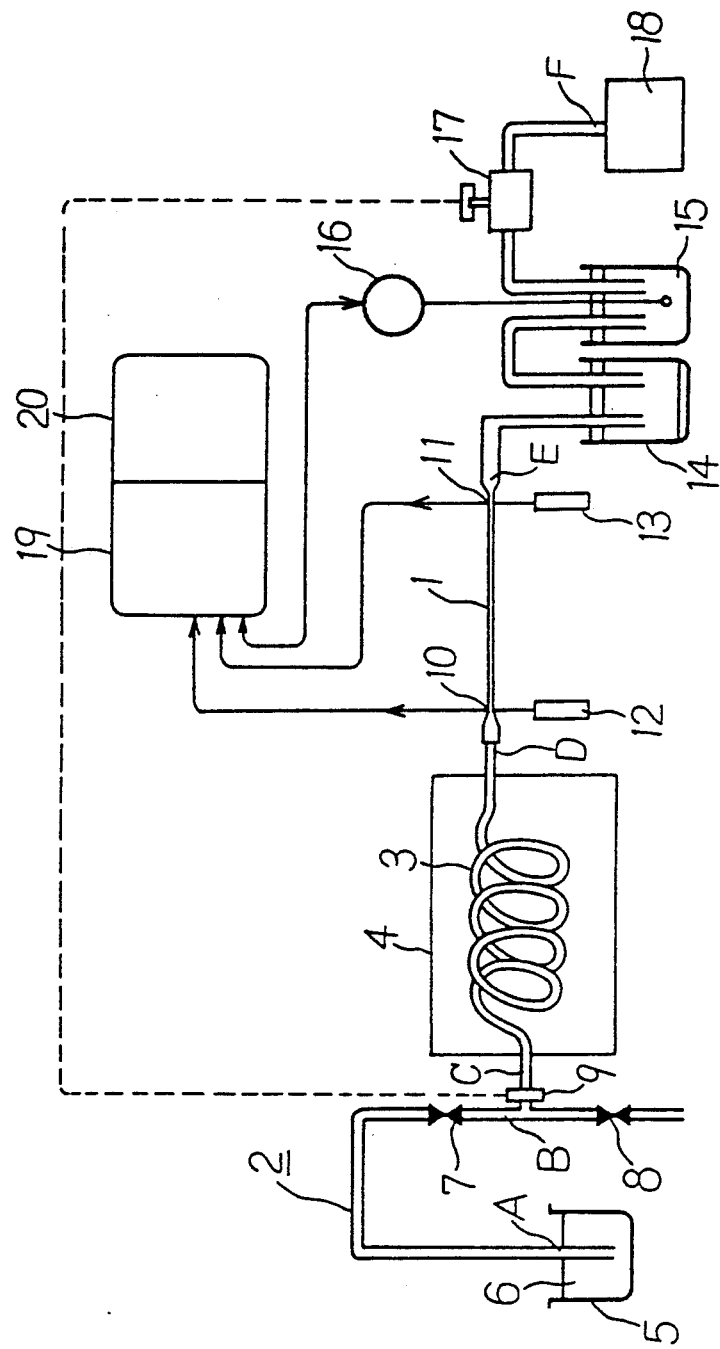
FIG. 1 is a combination of a schematic diagram and a block diagram showing the essential components and their organization of one example of a liquid viscometric apparatus constituting a preferred embodiment of this invention.

In the embodiment of a liquid viscometric apparatus according to this invention shown in FIG. 1, a narrow tube 1 for measurement comprising a capillary tube or the like is connected at its upstream end to the downstream end of a test liquid feed flow path 2. This flow path 2 is for feeding a test liquid whose viscosity is to be measured, such as blood. Narrow tubes 1 for measurement of different inner diameter are used depending on the estimated viscosity of the test liquid.

Figure 8:
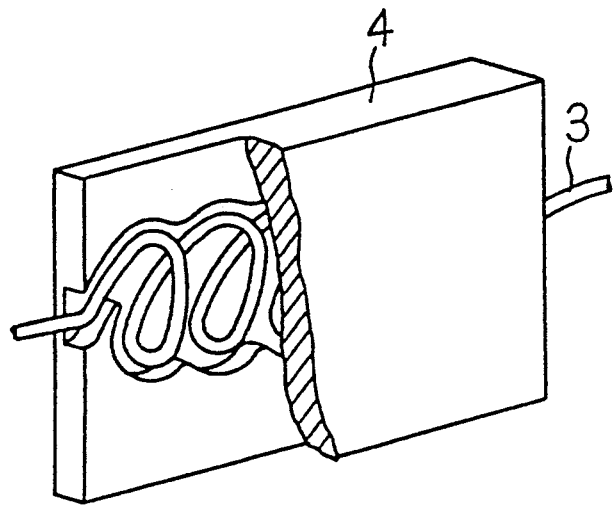
FIG. 8 is a perspective view, with one part cut away, showing a tubular flow path for retention imbedded in an electronic thermostatic plate.

A tubular flow path 3 for retention of coil form for the purpose of uniformizing the temperature of the test liquid is formed in the flow path 2 upstream of the narrow tube 1 for measurement. This tubular flow path 3 for retention is imbedded in an electronic thermostatic plate 4 constituting a thermostatic means as shown in detail in FIG. 8. This electronic thermostatic plate 4 has heating means and cooling means (not shown) for electrically controlling the temperature of imbedded tubular path 3 for retention at a set value.

The tubular flow path 3 for retention is made of a flexible material such as teflon. This tubular flow path 3 is imbedded in and fixed to the electronic thermostatic plate 4. By this construction, any extension or contraction of the tubular flow path 3 for retention will not affect the narrow tube 1 for measurement even if there is a temperature variation.

In the case where a test liquid 6 has a high chemical reactivity, it is desirable that the tubular flow path 3 for retention be fabricated of a material of low chemical reactivity such as stainless steel.

On the upstream side of the tubular path 3, a test liquid tank 5 is provided for storing the test fluid 6. The test liquid 6 in this tank 5 is under atmospheric pressure. One end (the upstream end) of the aforementioned test liquid feed flow path or piping 2 is inserted into the test liquid tank 5. This piping 2 from the test liquid tank 5 to the tubular flow path 3 is provided therein with a test liquid supply valve 7 for opening and closing the flow path of the liquid 6 and a distilled water supply valve 8 for opening and closing the inlet path of distilled water for cleaning the entire piping 2. An inlet means 9 is communicatively connected at its upstream side to the portion of the piping 2 between the test liquid supply valve 7 and the distilled water supply valve 8. The downstream side of this inlet means 9 is connected to the upstream end of the tubular flow path 3 for retention. The inlet means 9 is provided with a photoelectric element for detecting the flow past of the test liquid 6 supplied from the tank 5 to the flow path 3.

Figure 5:
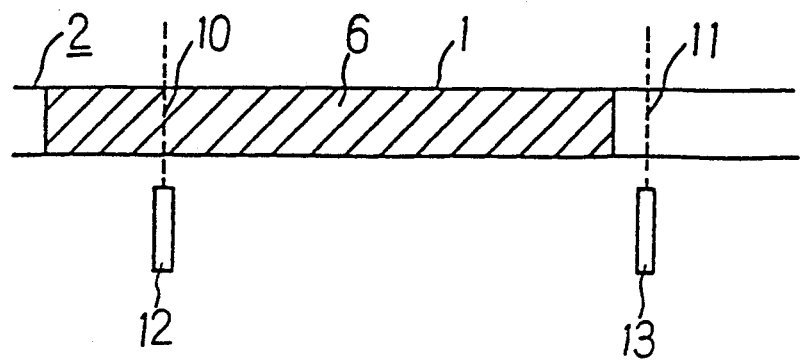
FIG. 5 is a simplified side view, in section, indicating a method of detecting the passing by of a leading part or a trailing part of a test liquid at a first position and a second position of a narrow tube for measurement.

Furthermore, the aforementioned narrow tube 1 for measurement has near its upstream and downstream ends a first position 10 and a second position 11, respectively. A first sensor 12 for detecting the time instant at which a specific part of the test liquid 6 flows past the first position 10 is provided at the first position 10. A second sensor 13 for detecting the time instant at which that part of the test liquid 6 flows past the second position 11 is provided at the second position 11. The first and second sensors 12 and 13 are respectively provided with photoelectric elements. Thus, the first and second sensors 12 and 13 detect the passing by of the leading part or the trailing part of a certain body of the test liquid 6 as indicated in FIG. 5. The volume of the test liquid 6 flowing through the flow path 2 is, for example, approximately 0.5 cc. Considering the narrow tube 1 to have a generally standard inner diameter, the length of test liquid 6 as shown in FIG. 5 is of the order of approximately 30 cm.

In the flow path 2 on the downstream side of the narrow tube 1 for measurement, a discharged liquid bottle 14 for receiving the test liquid 6 and a constant-pressure tank 15 having a buffer function for maintaining constant pressure are connected in series. The sensing part of a vacuum gauge 16 is installed within the constant-pressure tank 15 as a pressure measuring means for measuring the degree of vacuum within the interior of the tank 15.

By means of this vacuum gauge 16, the differential pressure between the pressure in the test liquid tank 5 under atmospheric pressure, i.e., the pressure on the upstream side of the narrow tube 1 for measurement, and the pressure within the constant-pressure tank 15, i.e., the pressure on the downstream side of the narrow tube 1 for measurement, is measured.

The starting and stopping of the measurement of the differential pressure by the vacuum gauge 16 are carried out as follows. The starting is triggered by the detection by the first sensor 12 of the passing by of the leading part or the trailing part of the test liquid 6 in the narrow tube 1, and measurement is carried out at specific divided time intervals. The stopping is triggered by the detection by the second sensor 13 of the passing by of the leading part or the trailing part of the test liquid.

These time intervals correspond to incremental divided time periods resulting from the division of the liquid passing-by time period for the test liquid 6 to pass by the second position 11 on the downstream side after passing by the first position 10 on the upstream side in the narrow tube 1 for measurement. Actually, the magnitude of each of these divided time periods is so set that it will be amply shorter than the time width corresponding to the width (amplitude) of fluctuation of the allowable differential pressure and is not directly dependent on the length (long or short) of the liquid pass-by time period.

Furthermore, on the downstream side of the constant-pressure tank 15 is connected, by way of a regulating valve 17, a vacuum pump 18 as differential pressure creating means for creating the differential pressure between the upstream and downstream sides of the narrow tube 1 for measurement.

The differential pressure between the upstream and downstream sides of the narrow tube 1 for measured is regulated by adjustment of the degree of opening of the regulating valve 17. This differential pressure is related to the passage time for the test liquid 6 to pass through the tubular flow path 3 for retention imbedded in the electronic thermostatic plate 4.

This passage time differs according to the viscosity of the test liquid 6 even if the suction due to the vacuum pump 18 is the same, that is, even if the differential pressure P is the same. The lower the viscosity, the shorter this passage time tends to become.

This passage time must be set at an ample length so that, as the test liquid 6 flows through the tubular flow path 3 for retention, it assumes an amply uniform temperature of, for example, 20 degrees C. On the other hand, if this passage time is unnecessarily long, the time period for the test liquid to pass through the narrow tube 1 will become long, and efficient measurement cannot be carried out.

Therefore, in order to carry out efficient measurement, this passage time is set at a minimum length at which the temperature of the test liquid 6 will become amply uniform while the test liquid is passing through the tubular flow path 3 for retention. The degree of opening of the regulating valve 17 must be set for each test liquid 6 in accordance with the magnitude of the viscosity thereof.

More specifically, the degree of opening of the regulating valve 17 is set in the following manner. First, with the apparatus in a state wherein the test liquid supply valve 7 is open and the distilled water supply valve 8 is closed, the regulating valve 17 is opened suitably and the test liquid 6 is drawn from the test liquid tank 5 by means of the vacuum pump 18. Then the arrival of the leading part of the flow of the test liquid 6 at the inlet means 9 is detected by the aforementioned photoelectric element provided at the inlet means 9, and the time for the test liquid 6 to move from the test liquid tank 5 to the inlet means 9 is measured. The degree of opening of the regulating valve 17 is so adjusted for each test liquid 6 that this measured moving time becomes a specific predetermined time. In this manner, the higher the viscosity of the test liquid 6, the higher is the impressed differential pressure.

In the case where the viscosity of a test liquid 6 of a different kind is to be measured, first, the test liquid supply valve 7 is closed, and the distilled water supply valve 8 is opened. Thus distilled water is introduced into the flow path 2 to clean the same. Then the test liquid supply valve is opened, and the distilled water supply valve 8 is closed. The new test liquid 6 is then caused to flow through the flow path 2.

Furthermore the liquid viscometric apparatus is provided with a flow rate computing means 19, into which signals from the first and second sensors 12 and 13 and from the vacuum gauge 16 are inputted. This flow rate computing means 19 thus operates to determine the product of the differential pressure measured for each of the aforementioned divided time periods by the vacuum gauge 16 and the divided time periods and to integrate this product over the liquid pass-by time thereby to obtain an integrated quantity by computation.

In addition, a viscosity computing means 20 is provided to compute the viscosity of the test liquid 6 by comparing an integrated quantity previously determined with respect to a reference sample liquid under the same conditions by the flow rate computing means 19 and the integrated quantity determined with respect to the test liquid 6 by the flow rate computing means 19, thereby to compute the viscosity of this test liquid 6.

Figure 7:
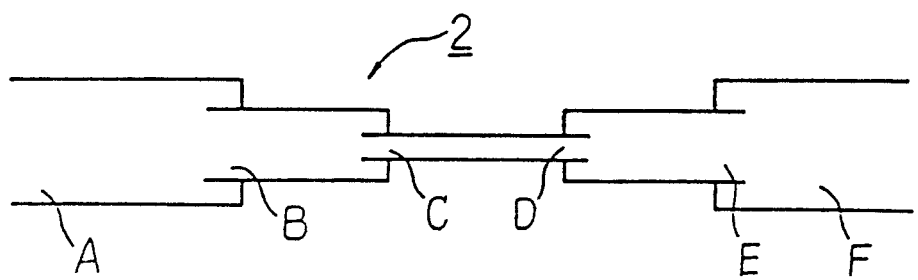
FIG. 7 is a simplified side view showing an example of a flow path comprising tubes of different inner diameter, in which reference characters A, B, ... E, F correspond to reference characters A, B, ... E, F in FIG. 1.

The test liquid flow path 2 comprises tubing of the following relative inner diameters. The flow path 2 in its portion from a position A near the test liquid tank 5 to a position B near the inlet means 9 as shown in FIGS. 1 and 7 comprises a pipe of large inner diameter. The flow path 2 from the position B to a position C near the inlet of the tubular flow path 3 for retention is formed by a pipe of intermediate inner diameter. From the position C to a position D near the outlet of the tubular flow path 3 for retention, the flow path 2 is formed by a pipe of small inner diameter. From the position D to a position E near the outlet of the narrow tube 1 for measurement, the flow path 2 comprises a pipe of intermediate inner diameter. From the position E to a position F near the vacuum pump 18, the flow path 2 is formed by piping of large inner diameter.

The diameters of these pipes and tubes constituting the flow path 2 differ with the magnitude of the viscosity of the test liquid 6. For example, in the case of a test liquid of low viscosity such as water: the inner diameter of the pipe of large diameter is approximately 3 mm; the inner diameter of the pipe of intermediate size is approximately 1 mm; and the inner diameter of the pipe of narrow size is approximately 0.5 mm. For measurement of a fluid of high viscosity such as grease: the large pipe inner diameter is approximately 10 mm; that of the intermediate-size pipe is approximately 3 mm; and that of the narrow pipe is approximately 1.5 mm.

Thus the inner diameter of the flow path 2 increases in the upstream direction from the tubular flow path 3 for retention. It increases also in the downstream direction from the flow path 3 for retention. Moreover, the inner diameter of the narrow tube 1 for measurement is of intermediate size. The reason for the selection of this inner diameter distribution is as follows.

Figure 6A:
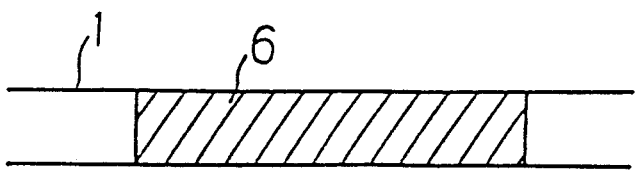
FIGS. 6a, 6b, and 6c are simplified side views, in section, indicating separations of the test liquid at a leading part or a trailing part of a test liquid in the case where the flow path of the test liquid does not comprise tubes of different inner diameters.
Figure 6B:
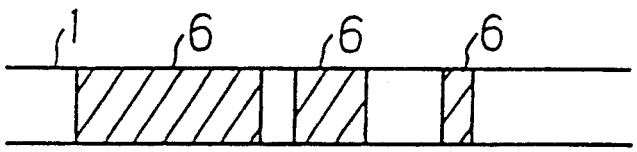
Figure 6C:
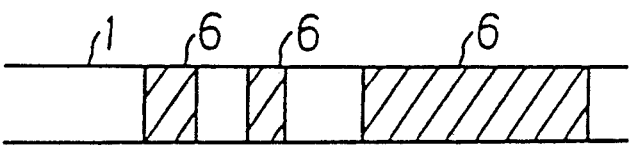

When experiments were carried out with a flow path 2 of uniform or constant inner diameter, the following results were obtained. In the case where the differential pressure is not very high, the test liquid 6 flowing through the narrow tube 1 for measurement is a continuous liquid body as shown in FIG. 6(a). However, when the differential pressure becomes high, discontinuities or breaks occurred at the leading part of this test liquid 6 as shown in FIG. 6(b) or at the trailing part thereof as shown in FIG. 6(c). These undesirable results were particularly remarkable in the case of test liquids 6 of high viscosity.

However, further experiments with a flow path 2 of the aforedescribed inner diameter distribution, i.e., of increasing diameter in the upstream direction from the tubular flow path 3 and also in the downstream direction therefrom and, moreover, an intermediate diameter for the narrow tube 1 for measurement, indicated that discontinuities in the leading or trailing part of the test liquid 6 are effectively prevented.

The embodiment of the invention of the above described organization operates in the following manner.

Figure 3:
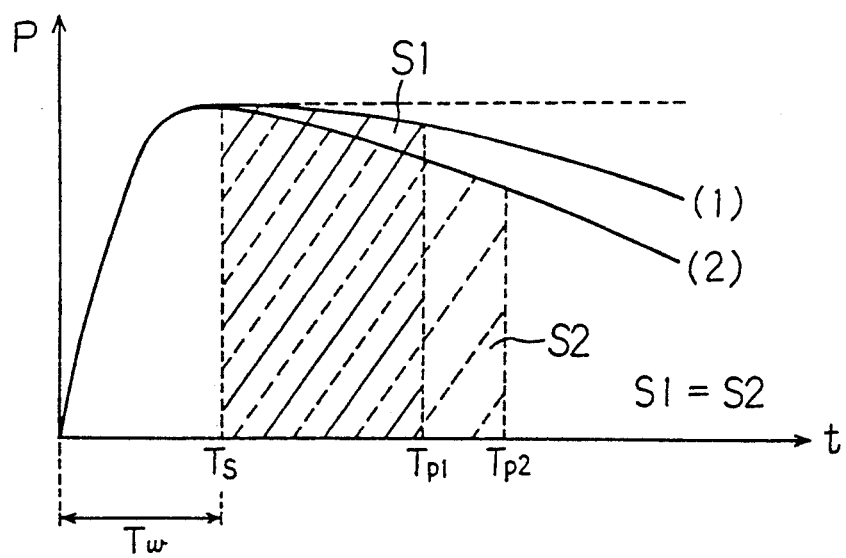
FIG. 3 is a graph indicating that integrated values S1 and S2 of the same test liquid are equal at (1) and (2) in the case where the manner of fluctuation of the differential pressure P differs.

In FIG. 3 the variation with time of value of the differential pressure P measured by the vacuum gauge 16 is indicated with respect to a case (1) and a case (2). In these cases (1) and (2): the test liquid 6 is the same specimen; the temperature conditions are the same; and the variation with time of the differential pressure P is different. In this graph, the time duration Tw denotes the waiting time for the test liquid within the electronic thermostatic plate 4 to attain an amply uniform temperature. The symbol $T_S$ denotes the instant of starting or departure, as measured by the first sensor 12, at which the trailing end (or the leading end) of the test liquid 6 passes by the first position 10 as shown in FIG. 5. The symbols $TP_1$ and $TP_2$ respectively denote the instants of arrival in cases (1) and (2), as measured by the second sensor 13, at which the trailing end (or the leading end) of the test liquid 6 in each case passes by the second position 11.

The differential pressure P in case (2) is lower than that in case (1). Accordingly the trailing end (or the leading end) of the test liquid 6 in case (2) passes by the second position 11 later than that in case (1). Therefore, $TP_2$ occurs later than $TP_1$. That is, the time period for passage of the test liquid 6 from the first position 10 to the second position 11 is longer in case (2) than that in case (1).

Figure 4:
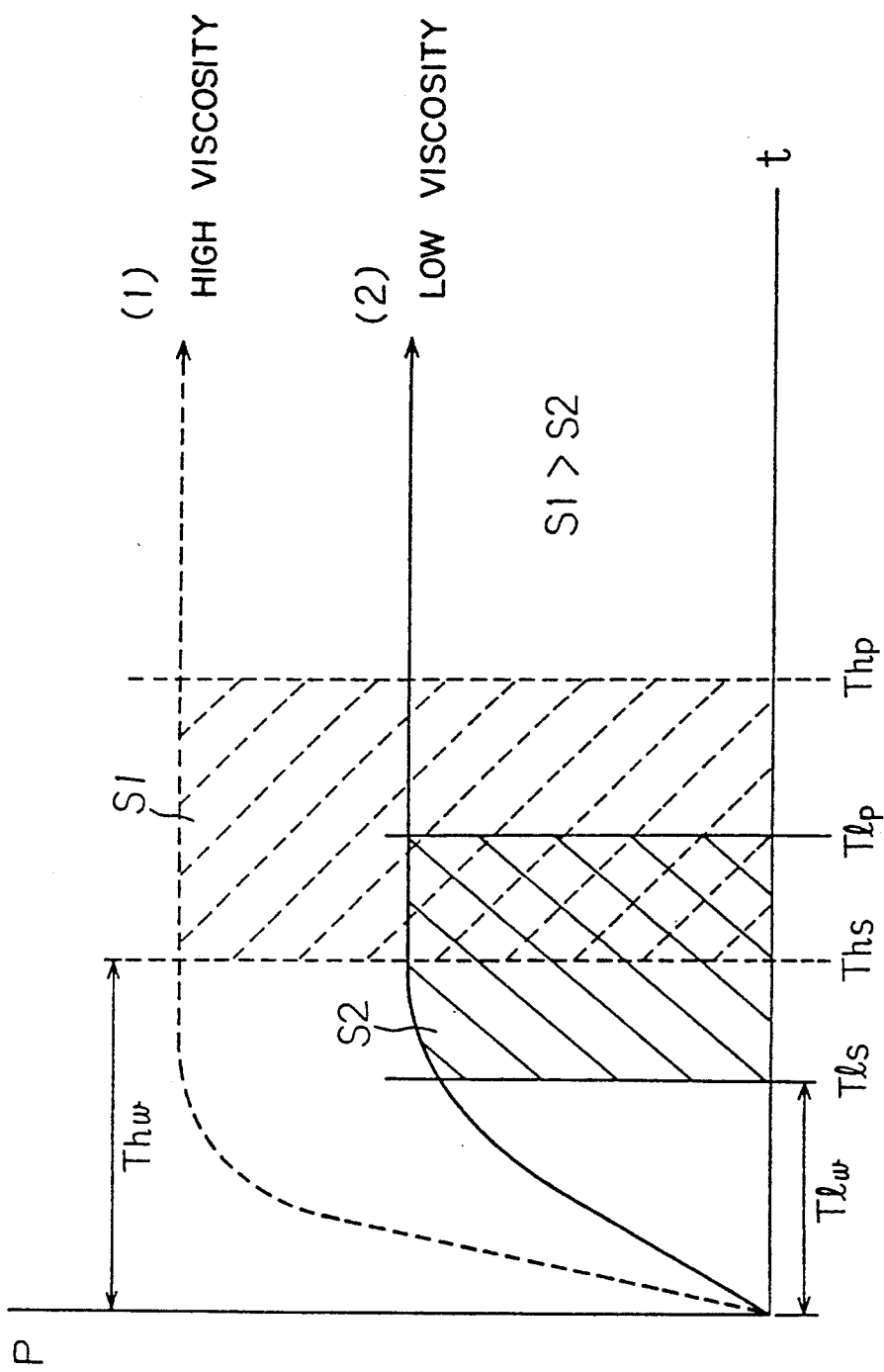
FIG. 4 is a graph indicating that the magnitudes of integrated values S1 and S2 of the test liquid are proportional to viscosity.

Experiments were carried out to determine the relationship between the integral S1 obtained by integrating the differential pressure from time instant $T_S$ to time instant $TP_1$ in case (1) and the integral S2 obtained by integrating the differential pressure P from instant $T_S$ to instant $TP_2$ in case (2). As a result it was confirmed that these integrals S1 and S2 are substantially equal. Furthermore, as indicated in FIG. 4, integrals S1 and S2 of the differential pressure P(t) from the starting instant $T_S$ to the arrival instant $T_P$ with respect to a high-viscosity test liquid (1) and a low-viscosity test liquid (2) of known viscosities were determined and compared. As a result it was verified that the integrals S1 and S2 were proportional respectively to their viscosities $\eta$. In each of these cases, the integral S is a quantity corresponding to the flow rate of the test liquid 6 passing by the first position 10 or the second position 11 in the time period from the starting instant $T_S$ to the arrival instant $T_P$.

Figure 9A:
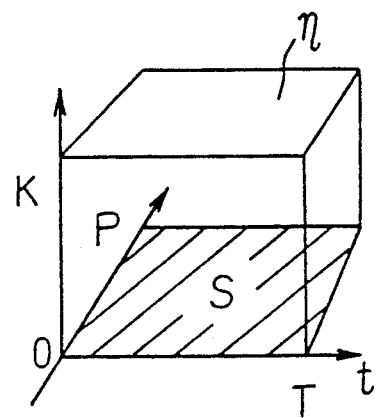
FIGS. 9a and 9b comprise three-dimensional graphical representations indicating that the viscosity of a liquid can be expressed as a volume which is the product of an integrated value and a proportional constant.
Figure 9B:
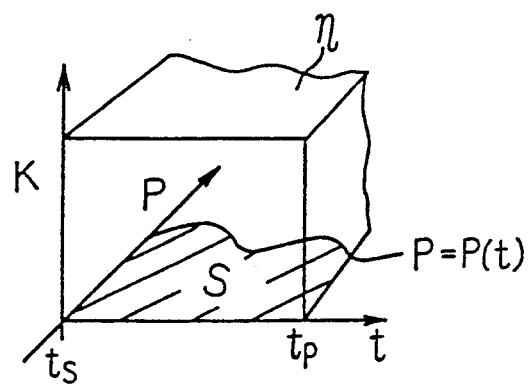

Therefore it was proved that the viscosity $\eta$ of the test liquid 6 is substantially proportional to the integral S of the differential pressure P(t) from the starting instant $T_S$ to the arrival instant $T_P$ as indicated by the following equation (1).

$$\eta = K \int_{t_S}^{t_P} P(t)dt \qquad (1)$$

where K is a proportionality coefficient depending on variables such as temperature. The purport of this equation (1) is conceptually indicated in FIGS. 9(a) and 9(b). As indicated in FIG. 9(a), the viscosity η is represented by a volume expressed by the product of the integral S and the proportionality coefficient K. Furthermore, as indicated in FIG. 9(b), in the case where the differential pressure P(t) fluctuates with time, also, the viscosity η can be represented by a volume expressed as the product of the integral S and the proportionality coefficient K.

Figure 2:
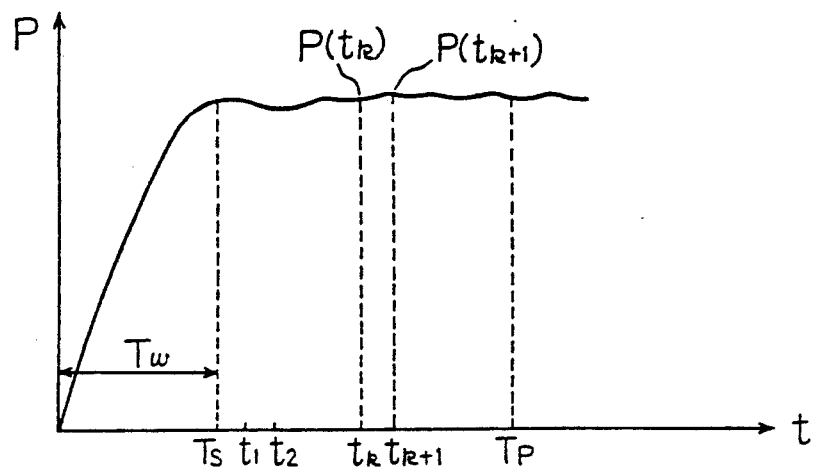
FIG. 2 is a graph indicating integration of differential pressure P over a time period extending from the time instant ($T_S$) at which a test liquid passes by an upstream first position to the time instant ($T_P$) at which the liquid passes by a downstream second position.

The integral S is specifically determined as indicated in FIG. 2 and the following equation (2).

$$\eta = K \sum_k P(t_k)(t_{k+1} - t_k) \tag{2}$$

The differential pressure P(t) is measured by means of the vacuum gauge 16 over the time instants $t_1, t_2, \ldots t_k, t_{k+1} \ldots$ from the starting instant $T_S$ to the arrival instant $T_P$ as indicated in FIG. 2 and equation (2). Then, by using the flow rate computing means 19, the products of the measured results $P(t_k)$ (k=1, 2, ... k+1, ...) and the divided time periods $(t_{k+1}-t_k)$ (k=1, 2, ... k, $k_{30\ 1}$, ...) are determined. By integrating these products, the integrated quantity S is determined.

Next, the procedure of determining the viscosity η of a test liquid 6 of unknown viscosity will be described.

First, the integral value S with respect to a reference sample liquid of known viscosity η is determined. Next, under the same conditions, the integral value S with respect to the test liquid 6, the unknown viscosity η of which is sought, is determined. Then, by utilizing the proportionality between the viscosity η and the integral value S, and by means of the flow rate computing means 19, the viscosity η of the test liquid 6 is determined by proportional calculation from the known viscosity of the reference sample liquid. In this connection, the integral value S with respect to the reference sample liquid of known viscosity η can be determined once under specific conditions, and the resulting data stored in the flow rate computing means 19. Then it will not be necessary to determine the reference integral value S for each measurement and determination of the viscosity of an unknown test liquid.

Furthermore, in order to obtain higher precision in the measurement of an unknown viscosity, it is also possible to use a plurality of reference sample liquids in the following manner. The integral value S of each of a plurality of reference sample liquids of known viscosities η is determined. The viscosity and integral value S of each reference sample liquid is stored. Then, by the use of these data and by, for example, the method of least squares, empirical formulas are obtained and stored in the flow rate computing means 19. These empirical formulas are obtained beforehand for each inner diameter of the narrow tube 1 for measurement or for each of different temperatures to be used. Then, the integral value S with respect to only the test liquid 6 of unknown viscosity η is determined. Finally, by using these empirical formulas thus previously stored, the unknown viscosity η is computed by proportional calculation or the like.

According to the organization of the present embodiment of the invention as described above, the unknown viscosity is determined, not by the time period per se for the test liquid to move from the first position 10 to the second position 11, but by the integral value S of the differential pressure P(t) over the time period from the starting time instant $T_S$ to the arrival instant $T_P$. For this reason, even if the differential pressure between the upstream side and the downstream side of the narrow tube 1 for measurement fluctuates, the unknown viscosity can be determined readily and accurately.

Another advantageous feature of the present invention is that discontinuities or breaks are prevented from occurring in the leading portion or the trailing portion of the test liquid flowing through the narrow tube 1 for measurement. This has been made possible by the increase in the inner diameter of the flow path piping in the upstream and downstream directions from the tubular flow path 3 for retention and by selecting an intermediate inner diameter for the narrow tube 1 for measurement.

Furthermore, a narrow tube 1 for measurement of narrow inner diameter is used for flow therethrough of the test liquid 6. Therefore, by changing the size of the inner diameter of this tube 1, measurement of test liquids of from low to high viscosities can be carried out.

Still another desirable feature of the present invention is that the tubular path 3 for retention is formed by a flexible material such as teflon and is imbedded in and fixed to an electronic thermostatic plate 4. For this reason, even if the temperature varies to cause the tubular path 3 to stretch or contract, the narrow tube 1 for measurement will not be affected.

A further feature of this invention is that a capillary tube can be used for the narrow tube 1 for measurement. For this reason, even in the case where only a small quantity of the test liquid 6 is used, its viscosity can be measured.

Furthermore, a differential pressure is applied to the test liquid 6 during measurement in order to increase its flow velocity. For this reason, the measurement time is shortened.

In the above described embodiment of the invention, a vacuum pump 18 was used on the downstream side as means for producing the differential pressure. However, the present invention is not thus limited. For example, a pressurizing means such as a compressor may be provided on the upstream side thereby to press on the test liquid 6 to cause it to flow for measurement.

Thus, as has been described above, the present invention is characterized by the provision of means for creating a differential pressure between the upstream and downstream sides of a narrow tube for measurement and flow rate computing means for integrating the products..of divided time periods and the respective differential pressures during these divided time periods over the period from the time instant at which the test liquid passes by the upstream first position in the narrow tube for measurement to the time instant at which the test liquid passes by the downstream second position thereby to compute an integral quantity. Therefore the viscosity of a test liquid of unknown viscosity can be readily determined with high precision and without being affected by any fluctuation of the differential pressure between the upstream side and the downstream side of the narrow tube for measurement.

What is claimed is:

1. Apparatus for measuring viscosities of liquids comprising:
    conduit means forming a flow path for a test liquid whose viscosity is to be measured;
    a narrow tube for measurement constituting an intermediate part of said conduit means and having upstream and downstream sides with respect to said flow path;

first and second detecting means for detecting the passing by of a specific part of said test liquid respectively past first and second positions in said narrow tube for measurement respectively near upstream and downstream ends thereof and for generating detection signals corresponding to said passing by;

differential pressure means for creating a differential pressure of said test liquid between said upstream and downstream sides;

pressure measuring means for measuring said differential pressure and generating a signal corresponding to said differential pressure at each instance of measurement;

flow rate computing means for computing an integrated quantity obtained by computing the total pass-by period for said specific part of the test liquid to flow between said first and second positions in response to said detection signals generated by said first and second detecting means, by dividing said total pass-by period into a plurality of divided time periods, by determining the product of each divided time period and the differential pressure thus measured in that divided time period in response to said signal generated by said pressure measuring means, and by integrating the products thus determined over said total pass-by period; and viscosity computing means for computing the viscosity of said test liquid by comparing said integrated quantity with a corresponding integrated quantity previously determined by said flow rate computing means under the same conditions with respect to a reference sample liquid of known viscosity.

2. Apparatus for measuring viscosities of liquids as claimed in claim 1 in which a tubular structure for retention of coil form for maintaining constant the temperature of said test liquid forms a portion of said conduit means upstream from said narrow tube for measurement and is imbeddedly enclosed in a thermostatic means.

3. Apparatus for measuring viscosities of liquids as claimed in claim 2 in which said tubular structure for retention is made of a flexible material.

4. Apparatus for measuring viscosities of liquids as claimed in claim 2 in which said tubular structure for retention is made of a low-reactivity material.

5. Apparatus for measuring viscosities of liquids as claimed in claim 2 in which said conduit means has inner dimension such that the cross-sectional area of said flow path increases in the upstream direction from the tubular structure for retention and increases in the downstream direction from the tubular structure for retention.

6. A method of measuring viscosities of liquids which comprises the steps of:

placing a test liquid whose viscosity is to be measured in a flow path formed by conduit means including at an intermediate portion thereof a narrow tube for measurement having upstream and downstream sides thereof with respect to said flow path;

applying a differential pressure to said test liquid between said upstream and downstream sides of said narrow tube for measurement thereby to cause the test liquid to flow through the narrow tube from the upstream side to the downstream side thereof;

measuring the total pass-by time period for said test liquid to pass by a second position on said downstream side after passing by a first position on said upstream side;

dividing said total pass-by time period into a plurality of divided time periods;

measuring said differential pressure during each of said divided time periods;

determining the product of each divided time period and the differential pressure measured in that divided time period;

integrating the products thus determined over said total pass-by time period thereby to obtain an integrated quantity; and computing the viscosity of said test liquid by comparing said integrated quantity with a corresponding integrated quantity previously determined under the same conditions with respect to a reference sample liquid of known viscosity.

7. A method of measuring viscosities of liquids as claimed in claim 6 in which said differential pressure is increased with increasing values of the viscosity of the test liquids.

* * * * *